United States Patent
Lee et al.

(10) Patent No.: US 11,234,993 B2
(45) Date of Patent: Feb. 1, 2022

(54) METHOD FOR TREATMENT OF CELLULAR SENESCENCE

(71) Applicant: National Yang Ming Chiao Tung, Taipei (TW)

(72) Inventors: Yi-Jang Lee, Taipei (TW); Yun-Lian Lin, Taipei (TW); Chung-Sheng Huang, Taipei (TW); Cheng-Han Tsai, Taipei (TW); Chun-Yuan Chang, Taipei (TW); Bing-Ze Lin, Taipei (TW); Yuan-Heng Tu, Taipei (TW); Wei-Hsiang Hsu, Taipei (TW); Pin-Ho Lo, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 16/883,380

(22) Filed: May 26, 2020

(65) Prior Publication Data

US 2020/0368264 A1    Nov. 26, 2020

Related U.S. Application Data

(60) Provisional application No. 62/851,761, filed on May 23, 2019.

(51) Int. Cl.
*A61K 31/7048* (2006.01)
*A61P 43/00* (2006.01)

(52) U.S. Cl.
CPC .......... *A61K 31/7048* (2013.01); *A61P 43/00* (2018.01)

(58) Field of Classification Search
None
See application file for complete search history.

(56) References Cited

U.S. PATENT DOCUMENTS 7,060,693 B1 * 6/2006 Dumas ................ A61Q 19/00
                                                514/170
8,574,852 B2    11/2013 Lee et al.

OTHER PUBLICATIONS

Chan, Y. Y., Wu, T. S., Kuoh, C. S., & Damu, A. G. (2005). A new phytoecdysteroid from Ajuga taiwanensis. Chemical and pharmaceutical bulletin, 53(7), 836-838. (Year: 2005).*
Arthur, S. T., Zwetsloot, K. A., Lawrence, M. M., Nieman, D. C., Lila, M. A., Grace, M. H., . . . & Shanely, R. A. (2014). Ajuga turkestanica increases Notch and Wnt signaling in aged skeletal muscle. Eur Rev Med Pharmacol Sci, 18(17), 2584-2592. (Year: 2014).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

* cited by examiner

*Primary Examiner* — Dale R Miller
(74) *Attorney, Agent, or Firm* — Muncy, Geissler, Olds and Lowe, P.C.

(57) ABSTRACT

The present invention provides an alcohol extract of *Ajuga taiwanensis* Nakai ex Murata exhibits significant effects on inhibiting the senescence in human WI-38 lung fibroblasts and human dermal fibroblasts. Moreover, the alcohol extract of *A. taiwanensis* is able to suppress the expression of the cofilin-1, a protein involved in actin dynamics and cell morphology and found to be increased in senescent cells. Suppression effect of cell senescence by this herb extract is more efficient in mild concentration without over-inhibition of cell viability and growth.

4 Claims, 8 Drawing Sheets
(4 of 8 Drawing Sheet(s) Filed in Color)

Fig. 2 (A)
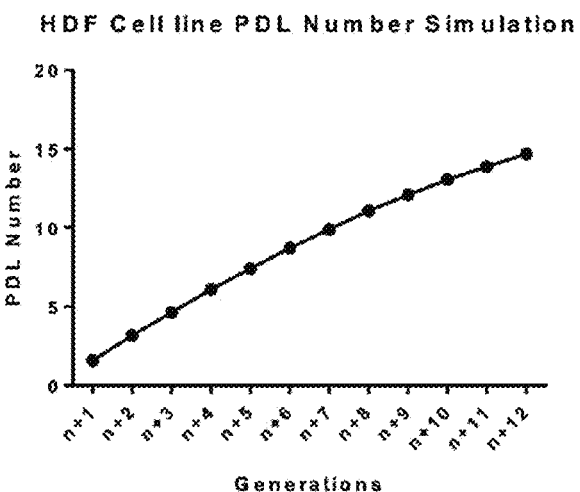
Fig. 2 (B)
Human Dermal Fibroblast Cell line
Young | old
Green: cellular F-actin
Blue: DPAI staining of the nucleus
Fig. 2 (C)
Young HDF cell (Pn+4)　Old HDF cell (Pn+12)
Fig. 2 (D)
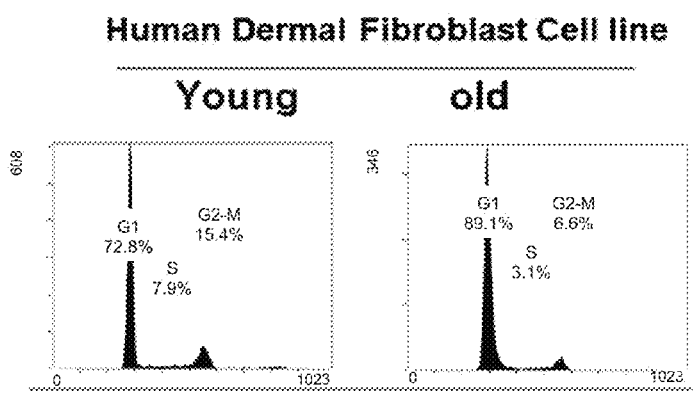
Fig. 2(E)
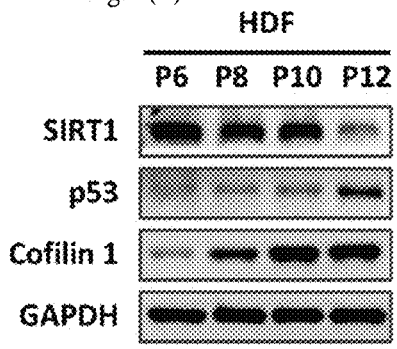

METHOD FOR TREATMENT OF CELLULAR SENESCENCE

BACKGROUND OF THE INVENTION

Technical Field of the Invention

The present invention relates to an *Ajuga taiwanensis* extract and using method thereof for treatment of cellular senescence. In particular, the method comprises administrating an effective amount of an anti-aging composition comprising alcohol extract of *A. taiwanensis* Nakai ex Murata to a subject.

Background

Cellular senescence is an irreversible physiological process because of the shortage of chromosomal telomeres accompanied by the continuously cell division. Additionally, cell shape becomes enlarged and flattens, as well as the entry of G0 phase of the cell cycle to prevent DNA from replication. Although it is inaccessible to directly control the shortage of telomeres in senescent cells, several efforts have been emphasized to replenish the senescent cells or remodel the cell shape using the growth factors that can temporarily reverse the senescent phenotypes.

The appearance of aging can be easily observed via the change of skin architecture, and it is an irreversible physiological process. Because the shortage of chromosomal telomeres accompanied by uninterrupted cell division, cell shape becomes enlarged and flattened. Cofilin-1, a molecule belongs to actin de-polymerization factor (ADF)/cofilin family, plays an important role in maintaining cell morphology. Although the underlying mechanisms are unclear, several lines of evidence have proved that the effects of expression level of cofilin-1 are associated with cellular senescence.

Cofilin-1 (CFL-1) is a small protein (~19 kD) that exists in eukaryotes and belongs to the actin depolymerization factor (ADF)/cofilin family (Wang H, et al. *Nucleic acids research*, 29(8):1653-1660, 2001). The ADF/cofilin protein family consists of ADF, CFL-1 and CFL-2. Both CFL-1 and ADF are non-muscle isoforms. However, CFL-1 is more abundant than ADF in mammalian cells. Deletion of CFL-1 gene leads to lethality in mouse, suggesting that the functions of CFL-1 and ADF are not redundant (Gurniak C B, Perlas E, & Witke W., *Developmental biology* 278(1):231-241, 2005). On the other hand, inhibition of ADF/cofilin family proteins also causes the failure of cell division but not chromosomal segregation in yeast, fruit fly, blastomere of *Xenopus* (Bamburg J R., *Annual review of cell and developmental biology* 15:185-230, 1999; Bamburg J R, McGough A, & Ono S., *Trends in cell biology* 9(9):364-370, 1999). The fundamental function of ADF/cofilin is to accelerate the turnover of actin filaments by depolymerizing or severing the actin filaments. Interestingly, CFL-1 enhances the actin polymerization for cell motility and other physiological behaviors instead of disrupting actin filaments (Elam W A, Kang H, & De la Cruz E M., *FEBS letters* 587(8):1215-1219, 2013). Cell mobility, morphology, cell cycle progression and cell division are all dependent on the activity of cofilin-1 to modulate the actin cytoskeleton. Therefore, the over-expression of cofilin-1 will promote cell senescence, and the suppression of cofilin-1 in senescent cells will reduce the senescent phenotypes. U.S. Pat. No. 8,574,852 discloses a method, comprising detecting the expression level of confilin-1 in a cell or tissue sample, for determining the cellular senescent condition in the cultured cell or the tissue sample.

The Chinese herb medicine has been considered as to maintain and regulate the normal physiology, including the replenishment of senescent cells. *Ajuga taiwanensis*, belonging to Lamiaceae, is a type of perennial herb. *A. taiwanensis* has been found in mainland China, Taiwan, Malaysia, and Africa. Whole plant of *A. taiwanensis* has been used for anti-inflammation, relieving swelling and redness. In Taiwan, *A. taiwanensis* is also used for treating goat, anti-diuretic, malaria, and inflammation related diseases. *A. taiwanensis* is known for containing sitosterol and phenolic compounds (Ardekani M S, et al., *Journal of Essential Oil Bearing Plants* 13(1):45-51, 2010; Manguro L O A, et al., *Journal of Asian natural products research* 9(7):617-629, 2007) and different kinds of neo-clerodane diterpenes (Chiou et al., *Phytochemistry* 80:64-69(2012; Castro et al., *J Nat Prod* 74:1036-1041, 2011) and phytoecdysteroid (Chan et al., *Chem Pharm Bull.* 53:836-838.) However, there is no evidence or disclosure mentioned that *A. taiwanensis* possesses effects of anti-aging, whitening, or moisturizing. In the present invention, it is verified that *A. taiwanensis* is able to suppress cofilin-1 expression accompanied by reducing the level of senescence associated-galactosidase (SA-β-gal) in human dermal fibroblasts, which suggests that *A. taiwanensis* should possess effects on preventing and/or treatment of cellular senescence.

SUMMARY OF INVENTION

In one aspect, the present invention provides an alcohol extract of *A. taiwanensis* (ATE) which is able to reverse the senescent phenotypes temporarily and decrease the cofilin-1 levels in human dermal fibroblasts (HDF) model, which is established to evaluate the senescence by population doubling level formula (PDL). In one embodiment, the component of ATE is analyzed by high performance liquid chromatography (HPLC) and shows that it contains an active compound called 8-O-acetylharpagide.

In one embodiment of present invention, it shows that ATE exhibits significant effects on inhibiting the senescence in human dermal fibroblasts. In one preferred embodiment, the PDL is 3.32×log (Xe/Xb)+S, wherein Xb is the cell number at the beginning of the incubation time, Xe is the cell number at the end of the incubation time, and S is the PDL of starting time point. In another preferred embodiment, the PDL formula is n=3.32 (log UCY−log I)+X, wherein n is the final PDL number at end of a given subculture, UCY is the cell yield at that point, I is the cell number used as inoculum to begin that subculture, and X is the doubling level of the inoculum used to initiate the subculture being quantitated.

In one embodiment, ATE suppresses the expression of the cofilin-1, a protein involved in actin dynamics and cell morphology and found to be increased in senescent cells. Also, it is found that ATE can restore the expression of a longevity gene, SIRT1, in senescent cell.

In other embodiments, the anti-aging effect of sub-fractions of ATE, comprising ethyl acetate-soluble, butanol-soluble, and water-soluble fractions, are also evaluated.

In another aspect, the present invention provides an anti-aging composition, comprising an alcohol extract of *A. taiwanensis* (ATE). In one embodiment of present invention, the senescent HDF cells are treated with different concentrations of the sub-fractions of ATE for 24 hours and then analyzed by SA-β-gal staining. The aging is improved by treating with the sub-fractions of ATE.

In another embodiment of present invention, the cell growth rate after treatment of ATE is increased.

In one embodiment of present invention, ATE inhibits or suppresses the expression of molecules in the cell cycle checkpoint, comprising p53, p27 and the aging-related molecule cofilin-1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A-2E show the human fibroblast cells (HDF) model is established to evaluate senescence. (A) Population doubling level formula is used to simulate HDF cell line growth. (B) Immunofluorescences staining is used to examine the distribution of the actin cytoskeleton and cell morphology in HDF cells. (C) Comparisons of cells morphology of young and senescent HDF cells. (D) The difference between cell cycles of young and senescent HDF cells. (E) The senescent-related molecular expression of p53 and cofilin-1 between young and senescent HDF cells.

FIG. 3 shows the cytotoxicity evaluation result of ATE. HDF cells are treated with different concentrations of ATE to verify if ATE is cytotoxic and $IC_{50}$ value.

DETAILED DESCRIPTION OF THE INVENTION

Figure 1:
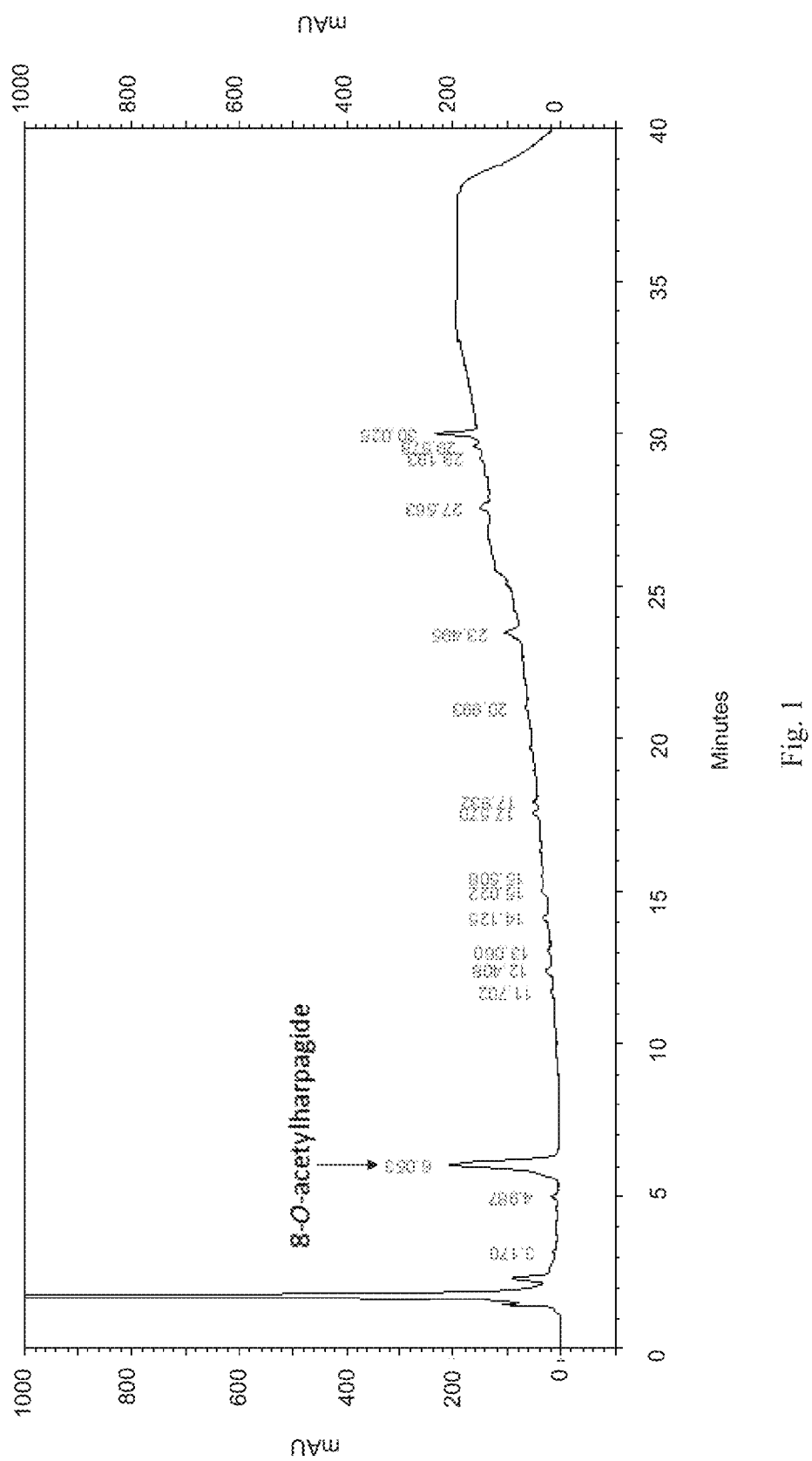
FIG. 1 shows the HPLC analysis of ATE.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

EXAMPLES

The other characteristics and advantages of the present invention will be further illustrated and described in the following examples. The examples described herein are using for illustrations, not for limitations of the invention.

The practice of the present invention will employ technologies comprising conventional techniques of cell biology and cell culture, which are within the ordinary skills of the art. Such techniques are explained fully in the literature Human Dermal Fibroblasts (HDF) Model Human dermal fibroblasts, HDF cells (ATCC® PCS-201-010™) are cultured in Fibroblast Growth kit-Low serum (ATCC PCS-201-041) with 2% fetal bovine serum and used standard culture conditions (37° C., 95% humidified air and 5% $CO_2$). HDF cells are cultured every 48 hours, and cells are getting older after every passage. The population doubling level (PDL) formula is according to American Type of Culture Center, ATCC. PDL=3.32×log (Xe/Xb)+S, wherein Xb is the cell number at the beginning of the incubation time, Xe is the cell number at the end of the incubation time, and S is the PDL of starting time point. And the PDL formula is n=3.32 (log UCY−log I)+X, wherein n is the final PDL number at end of a given subculture, UCY is the cell yield at that point, I is the cell number used as inoculum to begin that subculture, and X is the doubling level of the inoculum used to initiate the subculture being quantitated.

Preparation of ATE and the Sub-Fraction Thereof

The dried aerial parts of *A. taiwanensis* is ground and extracted with aqueous ethanol (80%) and concentrated under reducing pressure to yield a crude extract (ATE). The crude extract is suspended in water and then partitioned sequentially with ethyl acetate (EA) and butanol (BuOH) to obtain the EA, BuOH and $H_2O$-soluble fractions, respectively. Each fraction is used for following experiments.

Cell Growth Curves Analysis

First of all, HDF cells are seeded ($10^5$ cells) in 60-mm culture dish and incubated at 37° C., 95% humidified air and 5% $CO_2$ for 24 hours. And then HDF cells are treated with ATE in two concentrations, 50 and 100 μg/ml for 24 hours. After trypsinization, the cell number of each group is counted. The cell counting is conducted every day for 7 days.

MTT Assay

In one embodiment, MTT (3-(4,5-Dimethylthiazol-2-yl)-2,5-diphenyl-tetrazolium bromide) is used to test cells viability. HDF cells are seeded in 96-well plate (2000 cells/well). Each well is treated with different concentrations of ATE for 24 hours and replaced with 0.5 mM MTT serum free medium in 37° C. incubator for 4 hours. The medium is removed and then Dimethyl sulfoxide (DMSO) is added to form purple crystal. Finally, ELISA reader (TECAN) is used for measuring OD value under 570 nm wavelength.

In another embodiment, the same procedure is processed for evaluating the cytotoxicity of ATE-EA, ATE-BuOH, and ATE-$H_2O$ on HDF cells.

Senescence-Associated-β-Galactosidase (SA-β-Gal) Staining

Cells are fixed by using 0.2% glutaraldehyde plus 2% formaldehyde at 37° C. for 5 min, and then rinsed with phosphate buffered saline (PBS). The staining solution (1 mg/ml of 5-Bromo-4-chloro-3-indolyl β-D-galactopyranoside, 5 mM potassium ferricyanide, 5 mM potassium ferrocyanide, 150 mM NaCl, 1 mM $MgCl_2$, 40 mM citric acid (pH 6.0)) is added into the culture dishes and incubated at 37° C. for 24 hours. The stained cells are visualized under an optical microscope with digital camera (Olympus, Center Valley, Pa., USA). Quantification is determined by counting the number of positive stained cells per 100 randomly selected cells Western Blot Analysis Protein lysates are prepared with RIPA buffer (Thermo Scientific Inc., Waltham, Mass., USA) containing 1% protease inhibitor. An equal amount of total protein is subjected to SDS/PAGE and then transferred onto a nitrocellulose membrane (PALL Co., Port Washington, N.Y., USA). The blots are incubated with blocking buffer (TBS-T with 4% skim milk) at room temperature for 1 hour and then hybridized with primary antibodies overnight at 4° C. followed by the horseradish peroxidase-conjugated secondary antibody incubation. Signals are illuminated using Enhanced Chemiluminescence reagent (Bio-Rad Laboratories Inc., Hercules, Calif., USA) and recorded on an Image-Quant LAS-4000 imaging system (GE Healthcare, Chicago, Ill., USA)

Embodiment 1. Chromatography of ATE

The chemical profile of ATE is performed by HPLC on a Purospher® star RP-18 endcapped column (5 μm) (150×4.6 mm) and operated on Hitachi 5160. The mobile phase is composed of solvent A (0.2% $H_3PO_4$) and solvent B (MeOH) using a gradient program as follows: 0-5 min, 30% B; 5-20 min, 30-60% B; 20-30 min, 60-80% B; 30-35 min, 80% B at a flow rate of 1.0 ml/min. The injection volume and UV detector are set at 10 μl and 203 nm, respectively. The results show that there is a major component in ATE called 8-acetylharpagide (FIG. 1).

Embodiment 2. Establish the Human Dermal Fibroblast (HDF) Cell Model

The human dermal fibroblast cell model is established to evaluate the senescence of cells by using population doubling level formula (PDL) (FIG. 2A). Senescent HDF cells are flattening, enlarging, and proliferating slowly (FIG. 2C). Cell skeleton also expands with the increase of algebra (FIG. 2B). Furthermore, in addition to cell growth rate and cell morphology changes, the cell cycle distributions of young and aged cells are also evaluated. The young HDF cells G1/G0 stage ratio is 72.8%, and aged cells G1/G0 stage is increased to 89.1% (FIG. 2D). The result showed that there is an increased proportion of aging skin cells entering the cell stagnation. Moreover, Senescence-associated-β-Galactosidase staining is conducted to demonstrate that Pn+12 HDF cells really enter the aging stage. The senescent-related molecular expressions of p53 and cofilin 1 among P6, P8, P10 and P12 generation HDF cells are evaluated. The expression of p53 is the strongest in P12 generation HDF cells, and the expression of cofilin-1 is increasing as the aging of HDF cells (FIG. 2E).

Embodiment 3. The Cytotoxicity of ATE

The cytotoxicity of ATE on HDF cells is analyzed by using MTT assay. As shown in FIG. 3, the survival rate of HDF cells is even slightly increased in cells treated with low concentration of ATE (10 μg/ml and 100 μg/ml). Moreover, the semi-lethal concentration ($IC_{50}$) of ATE falls in about 1500 μg/ml, so 50, 100 μg/ml is selected to be used in this present invention.

Embodiment 4. The Effects of Anti-Aging of ATE

Figure 4:
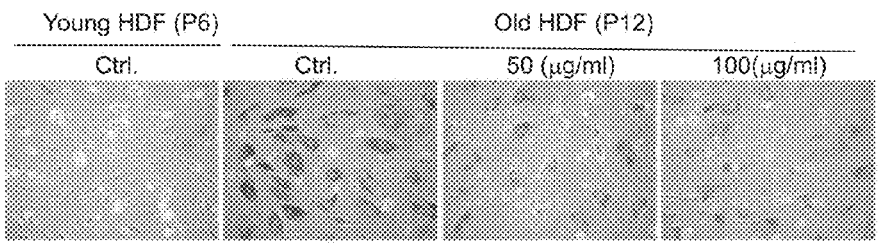
FIG. 4A-4G show the effects of anti-aging of ATE. HDF cells are co-cultured with different concentrations of ATE and stained by senescence-associated-β-Galactosidase (SA-β-gal). Also, senescent cells induced by BeSO4 and D-galactose are treated with different concentrations of ATE to see the change in SA-β-gal expression. (A) The comparison of SA-β-gal staining results between young HDF cells and senescent HDF cells treated with different concentration of ATE. (B) The quantification of SA-β-gal staining results. (C) Cell growth curve of young HDF cells and senescent HDF cells treated with different concentration of ATE (50 and 100 μg/ml). (D) The cell cycle distribution of HDF cells treated with ATE (100 μg/ml). (E) The SA-β-gal expression in senescent HDF cell after the treatment of ATE. (F) The SA-β-gal expression in senescence cell induced by BeSo4 after the treatment of ATE. (G) The SA-β-gal expression in senescent cell induced by D-galactose after the treatment of ATE.
Figure 4:
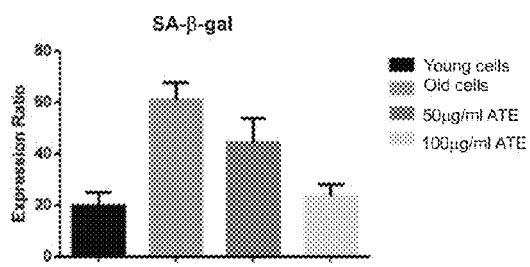
Figure 4:
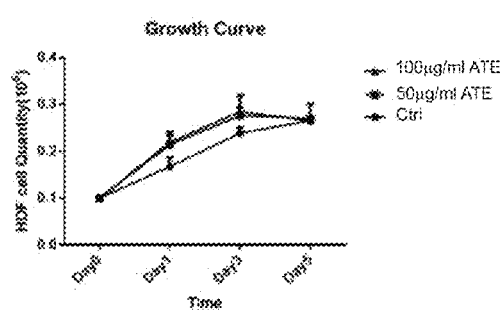
Figure 4:
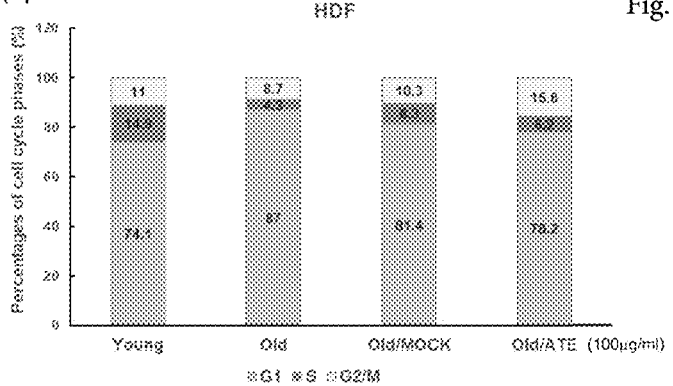
Figure 4:
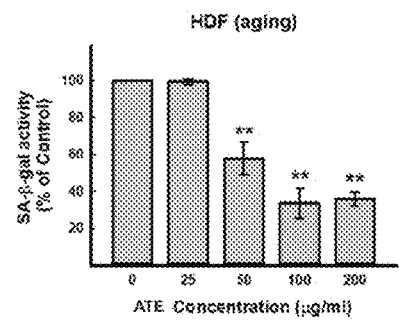
Figure 4:
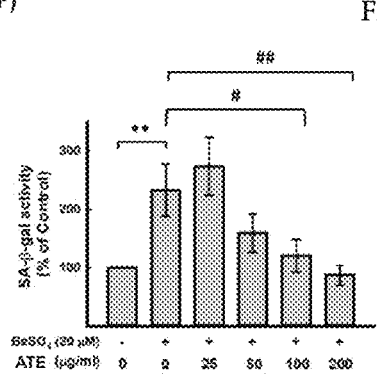
Figure 4:
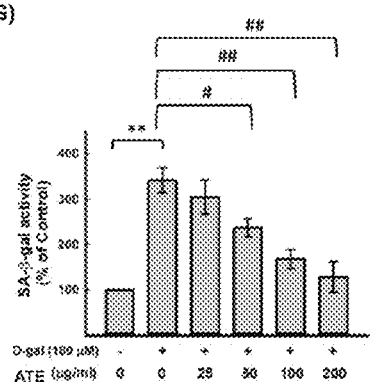

After establishing a young and senescent cell model and confirming that ATE is non-toxic, the effects of anti-aging of ATE are further evaluated. First, HDF cells are treated with 50 and 100 μg/ml of ATE for 24 hours and analyzed by SA-β-gal staining. The results show that the senescent cells after the treatment have a significant decrease in the amount of expression of SA-β-gal compared with the control group (FIG. 4A). It is more obvious from the quantitative results that both concentrations of the extract can reduce the amount of expression (FIG. 4B). And the effect of 100 μg/ml of ATE in inhibiting aging is better.

Next, the cell growth rate of the senescent cells treated with ATE is detected. The results show that the cell growth rate of the senescent cells treated with ATE is significantly higher than the control group, and the 50 and 100 μg/ml group achieved the same result (FIG. 4C). Although the growth rate of senescent cells cannot be reversed to as the normal cells, it shows that the treatment with ATE has a significant effect on slowing down aging and increasing cell growth.

In addition to using Senescence-associated-β-Galactosidase staining and observing changes in growth rate, the restoration of cell cycle is further evaluated. The results show that the G1/G0 phase of HDF cells treated with ATE is decreased from 85.2% to 75.3%, which is close to the 73.5% of the young group (FIG. 4D). It proves that ATE promotes the HDF cells resuming division and growth. And through the SA-β-gal expression evaluation, the treatment of ATE can decrease the expression of SA-β-gal in senescent HDF cells (FIG. 4E)

Furthermore, other senescence models are used for testing the anti-aging effect of ATE, for example, senescent cell induced by $BeSO_4$ and D-galactose. Like aforementioned procedures, two senescence cell models are treated with different concentrations of ATE for 24 hours, and then SA-β-gal expression of these two models is evaluated and quantified. As a result, SA-β-gal expression of the cell treated with ATE is decreased significantly (FIG. 4F-4G).

Embodiment 5. The Molecular Expression of HDF Cells Treated with ATE

Figure 5A:
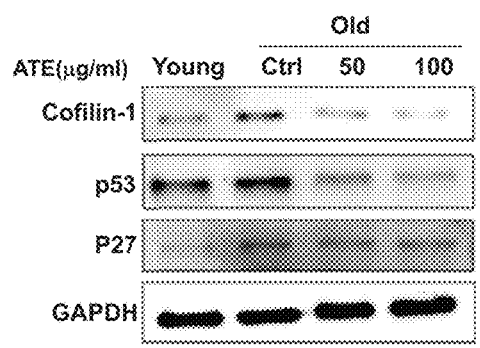
FIG. 5A-5D show the inhibition effect of ATE on senescent-related molecular, p53 and P27, and the increase effect of ATE on longevity marker SIRT1. (A) Western blot analysis is operated to evaluate the effect of ATE (50 and 100 μg/ml) in decreasing cofilin-1, p53 and p27 expression of HDF cell. (B) The quantitative results of western blot of cofilin-1, p53 and p27 expressed in HDF treated with different concentrations of ATE (50 and 100 μg/ml). (C) Western blot analysis is operated to evaluate the effect of ATE (50 and 100 μg/ml) in increasing SIRT1 expression of HDF cell. (D) The quantitative results of western blot of SIRT1 expressed in HDF treated with different concentrations of ATE (50 and 100 μg/ml).
Figure 5:
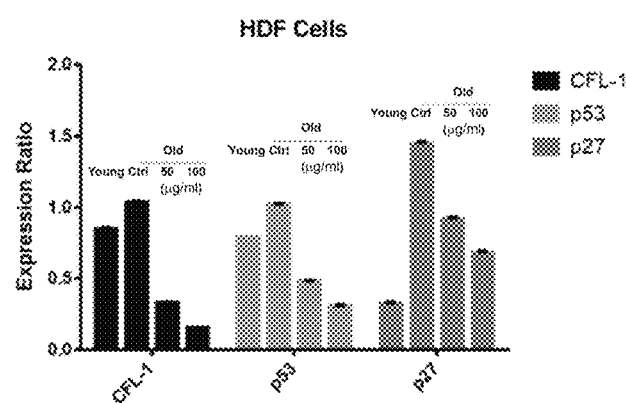
Figure 5:
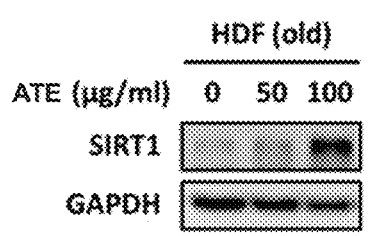
Figure 5:
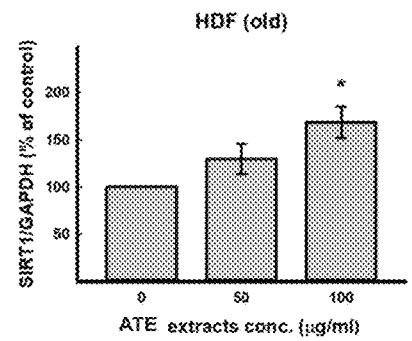

Senescent HDF cells can restore growth ability, increase growth rate, and re-enter cell division cycle by treating with ATE. Therefore, the molecules expressed in the cell cycle checkpoint, such as p53, p27 and the senescent-related molecule cofilin-1 are further evaluated. The results show that the expression levels of p53, p27 and cofilin-1 are significantly decreased after administration of 50 and 100 μg/ml of the ATE (FIGS. 5A and 5B).

On the other hand, the expression of longevity marker SIRT1 is also evaluated. The western blot analysis shows that ATE (50 and 100 μg/ml) increases SIRT1 expression in HDF cell (FIG. 5C). And the quantitative results of the SIRT1 western blot shows that the anti-aging effect of ATE in increasing the expression of SIRT1 is dose dependent (FIG. 5D).

Figure 6:
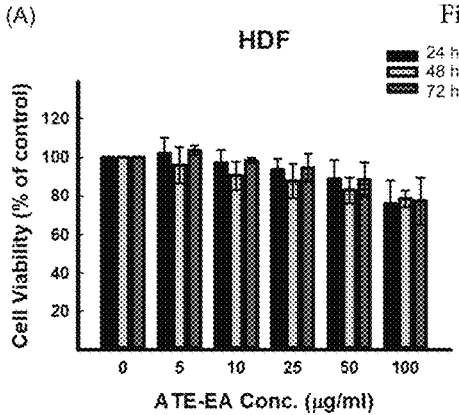
FIG. 6A-6F shows the cytotoxicity evaluation results of ATE sub-fractions on HDF cells and the cell proliferation rate of HDF cells after the treatment of ATE sub-fractions. HDF cells are treated with different concentrations of ATE sub-fractions, comprising ethyl-acetate (EA)-soluble fraction of ATE (ATE-EA), butanol (BuOH)-soluble fraction of ATE (ATE-BuOH), and water-soluble fraction pf ATE (ATE-H$_2$O), to verify the cytotoxicity and proliferation effect of the three ATE sub-fractions on HDF cells.
Figure 6:
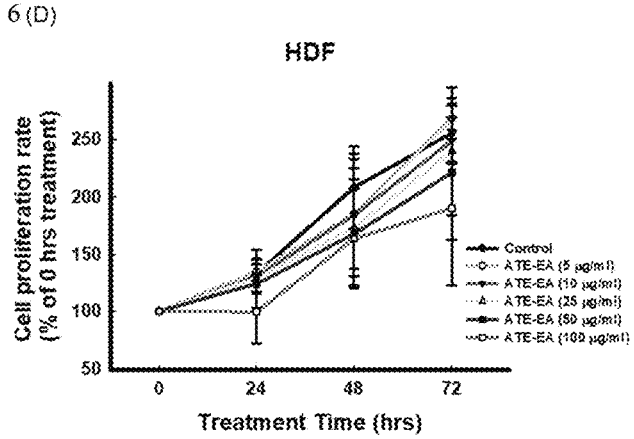
Figure 6:
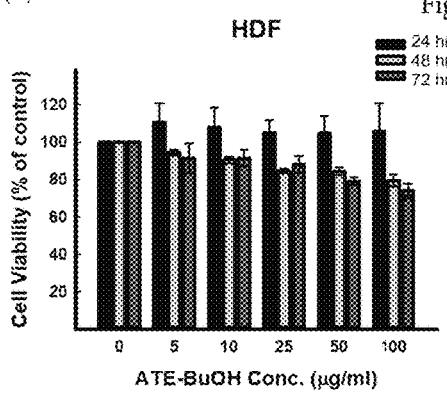
Figure 6:
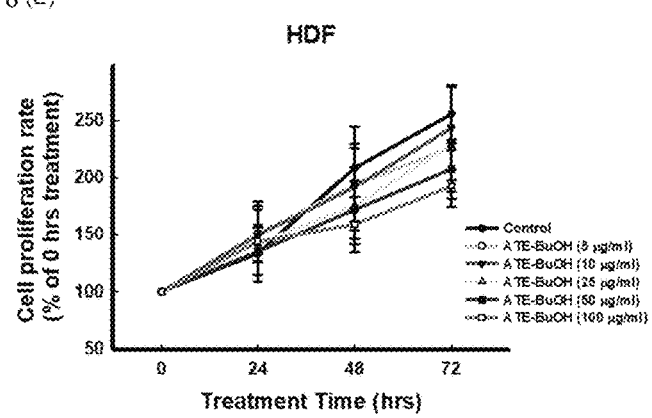
Figure 6:
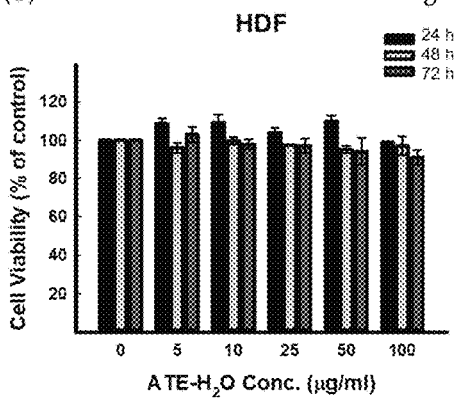
Figure 6:
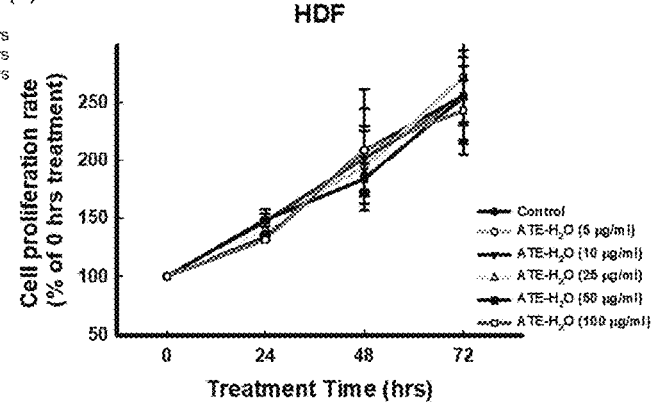

Embodiment 6. The Cytotoxicity of ATE Sub-Fractions on HDF Cells and the Cell Proliferation Rate of HDF Cells after the Treatment of ATE Sub-Fractions ATE is suspended in water and then partitioned sequentially with ethyl acetate (EA) and butanol (BuOH) to obtain the EA (ATE-EA), BuOH (ATE-BuOH) and $H_2O$-soluble (ATE-$H_2O$) fractions. The cytotoxicity of ATE sub-fractions on HDF cells is analyzed by using MTT assay. As shown in FIG. 6A-6C, the results indicate that the three sub-fractions of ATE, ATE-EA, ATE-BuOH, and ATE-$H_2O$, possess no cytotoxicity to HDF cells. Even when HDF cell is treated with the highest dose of three sub-fractions of ATE, the cell viability is still around 80%.

For the cell proliferation rate, the cell proliferation assay is performed by counting cell number for groups with or without the treatment of different concentrations of ABE sub-fractions at 24 hours to 72 hours. The hemocytometry is used to count the cell number, and the cell number of each time point is compared to initial seeded cell number (0 hour) to obtain the ratios. In conclusion, different concentrations (up to 100 mg/ml) of ABE sub-fractions do not cause significant cell death and inhibit cell proliferation rate (FIG. 6D-6F).

Embodiment 7. The Anti-Aging Effects of ATE Sub-Fractions

Figure 7:
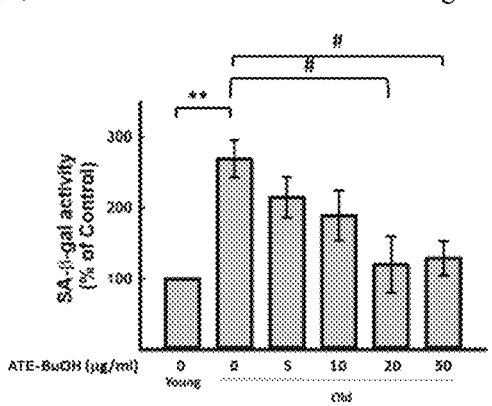
FIG. 7A-7E show the anti-aging effect of ATE-BuOH, ATE-EA and ATE-H$_2$O sub-fractions. (A) The SA-β-gal expression of HDF cell treated with different concentrations of ATE-BuOH. (B) The SA-β-gal expression of HDF cell treated with different concentrations of ATE-EA. (C) The SA-β-gal expression of HDF cell treated with different concentrations of ATE-H$_2$O. (D) The cofilin-1 and p53 expression of HDF cells treated with ATE-BuOH, ATE-EA and ATE-H$_2$O fractions are evaluated by Western blot analysis. (E) The quantitative comparison results of the SIRT1, p53, and cofilin-1 western blot between HDF cells treated with ATE-BuOH, ATE-EA and ATE-H$_2$O and control HDF cells.
Figure 7:
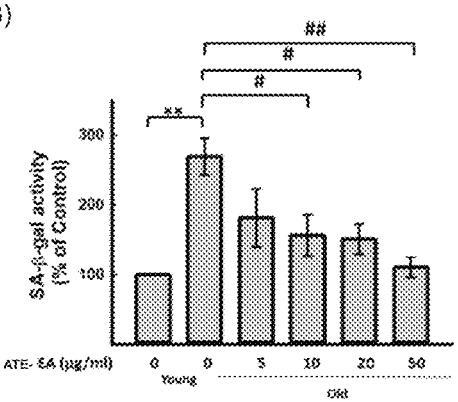
Figure 7C:
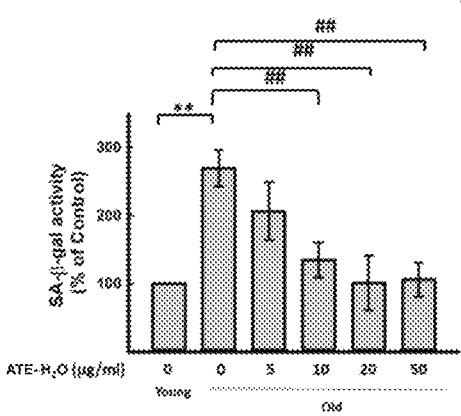
Figure 7D:
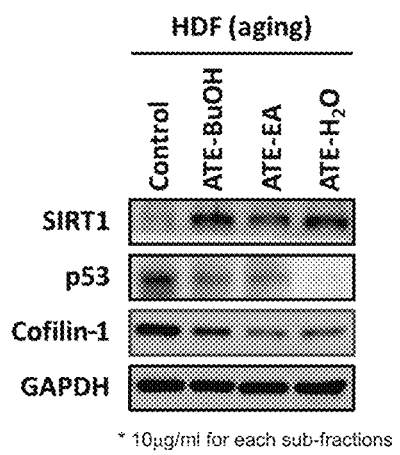
Figure 7:
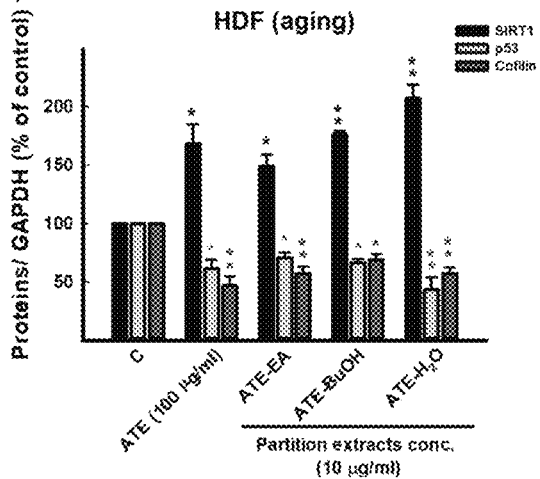
Figure 8A:
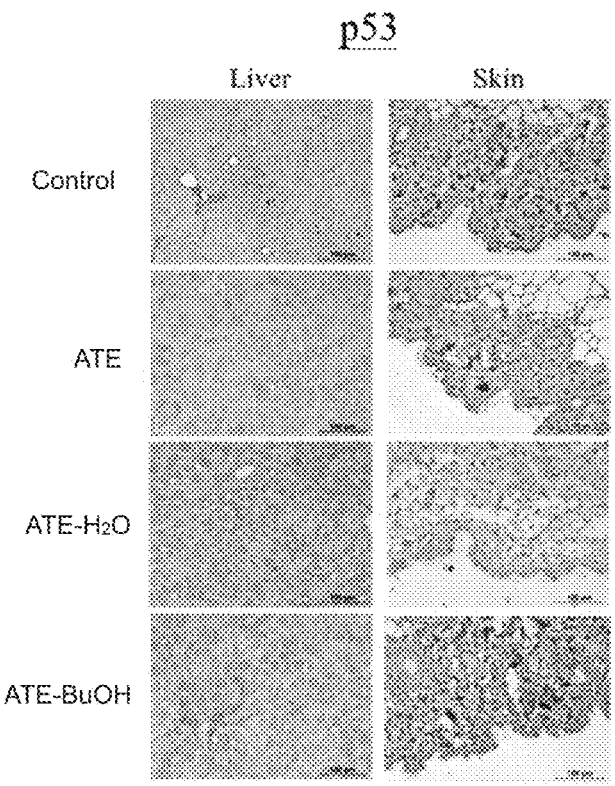
FIG. 8A-8C show the alterations of p53 expression in the mice treated with ATE, ATE-BuOH, ATE-H$_2$O and the water as control (Control). (A) The immunohistochemistry (IHC) staining for p53 of liver and skin tissues. (B) Quantification of the IHC staining intensity of skin p53. (C) Quantification results of the IHC staining intensity of liver p53.
Figure 8:
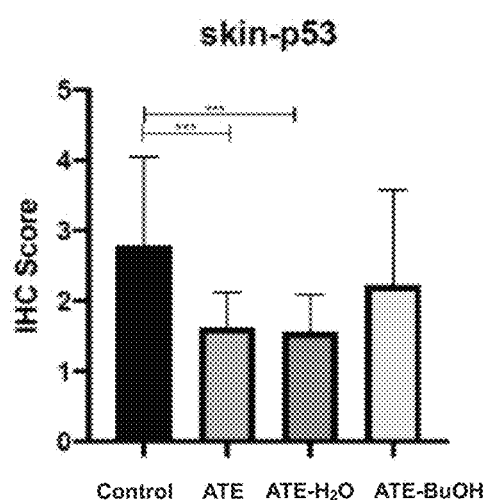
Figure 8C:
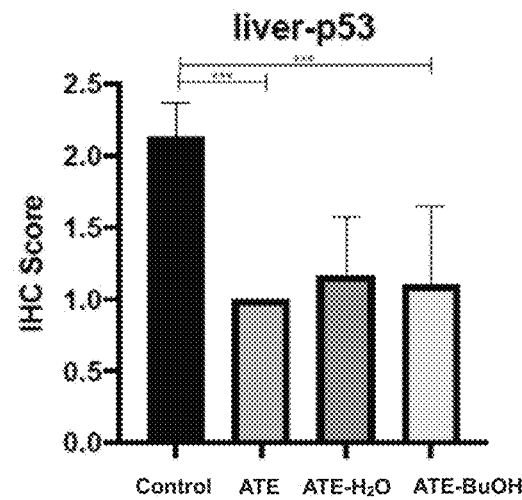
Figure 9:
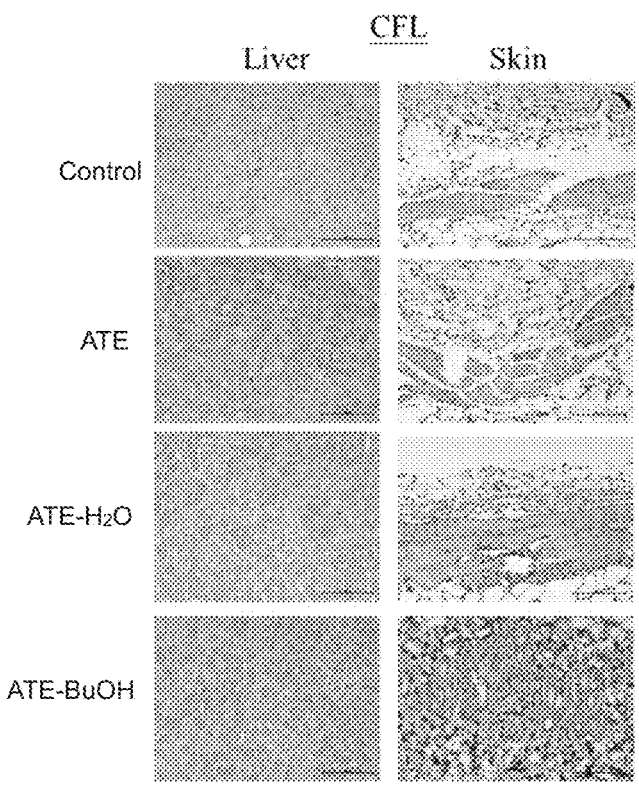
FIG. 9A-9C show the alterations of cofilin-1 (CFL) expression in the mice treated with ATE, ATE-BuOH, ATE-H$_2$O and the water as control (Control). (A) The IHC staining for CFL of liver and skin. (B) Quantification of the IHC staining intensity of liver CFL (C) Quantification results of the IHC staining intensity of skin CFL.
Figure 9:
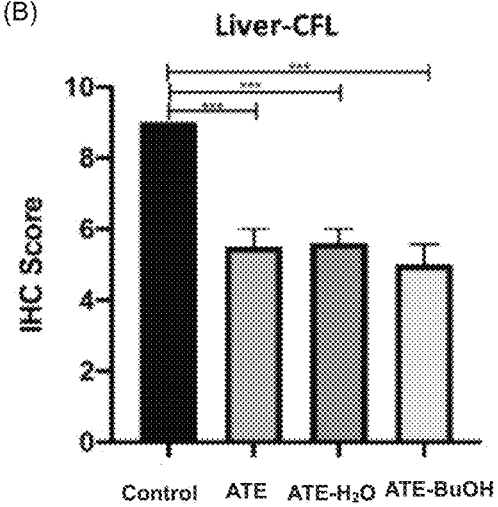
Figure 9:
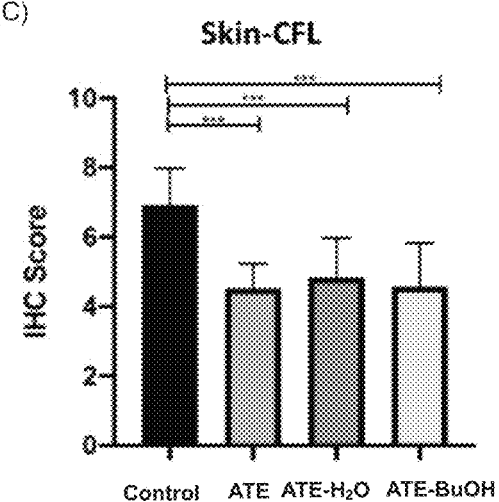

In additional, the anti-aging effects of sub-fractions of ATE are also evaluated. As shown in FIG. 7A-7C, the HDF cells are treated with ATE-BuOH, ATE-EA, and ATE-$H_2O$ sub-fractions to verify the anti-aging effects of these sub-fractions by SA-β-gal activity quantification. It shows that the sub-fractions of ATE also obtain the ability of anti-aging. Furthermore, the longevity marker SIRT1 and aging marker p53 and cofilin 1 expressed in HDF cell with or without ATE sub-fractions treatments are estimated by western blot (FIG. 7D). The quantification results of western blot indicate that the sub-fractions can increase the expression of SIRT1 and decrease the expression of p53 and cofilin 1 in HDF cell significantly, and the water sub-fraction is the most effective one among them (FIG. 7E).

Embodiment 8. Alterations of p53 and CFL-1 Expression in the Mice Treated with ATE and the Sub-Fractions of ATE There are 11-12 months old Balb/C mice considered as middle age model and used for evaluating the anti-aging effect of the ATE, ATE-$H_2O$ and ATE-BuOH. The mice are divided into four groups, control, ATE, ATE-$H_2O$ and ATE-BuOH, and fed respectively twice a day and five days per week for a month. Each of the groups has two mice and the dosages are 35 mg/kg of ATE per mouse, 7 mg/kg for each ATE-BuOH and ATE-$H_2O$. After the treatment, all the mice are sacrificed for p53 and cofilin-1 (CFL) IHC staining. As shown in FIG. 8A-8C and FIG. 9A-9C, IHC results of the liver and the skin indicate that ATE and the sub-fractions thereof can significantly decrease the expressions of both aging molecular markers, p53 and cofilin-1, compared to control group, except that the suppression ability of ATE-BuOH against p53 is weaker by comparison.

The invention claimed is:

1. A method for inhibiting senescence of human dermal fibroblasts comprising administering an effective amount of an anti-aging composition comprising an alcohol extract of *Ajuga taiwanensis*, as an anti-aging agent, wherein the alcohol extract comprises 8-O-acetylharpagide, to a subject need thereof.

2. The method of claim 1, wherein the anti-aging composition suppresses the expression of cofilin-1.

3. The method of claim 1, wherein the anti-aging composition suppresses the expression of p53, p27, ROS, or a combination thereof.

4. The method of claim 1, wherein the anti-aging composition increases the expression of SIRT1.

* * * * *